(12) United States Patent
Baur et al.

(10) Patent No.: US 9,226,943 B2
(45) Date of Patent: *Jan. 5, 2016

(54) LACTOBACILLUS JOHNSONII CNCM I-1225 FOR THE ANTI-ADHESION OF SKIN PATHOGENIC FLORA

(71) Applicant: NESTEC S.A., Vevey (CH)

(72) Inventors: Markus Baur, Aran (CH); Ralf Zink, Le Mont Pelerin (CH); Isabelle Auzanneau, Opio (FR); Karine Buffard, Fayence (FR)

(73) Assignee: Nestec S.A., Vevey (CH)

( * ) Notice: Subject to any disclaimer, the term of this patent is extended or adjusted under 35 U.S.C. 154(b) by 182 days.

This patent is subject to a terminal disclaimer.

(21) Appl. No.: 14/083,098

(22) Filed: Nov. 18, 2013

(65) Prior Publication Data

US 2014/0079677 A1    Mar. 20, 2014

Related U.S. Application Data

(60) Continuation of application No. 11/217,930, filed on Sep. 1, 2005, now Pat. No. 8,685,389, which is a division of application No. 10/177,589, filed on Jun. 21, 2002, now abandoned, which is a continuation of application No. PCT/EP00/12719, filed on Dec. 13, 2000.

(30) Foreign Application Priority Data

Dec. 22, 1999    (EP) .................................... 99204489

(51) Int. Cl.
| | | |
|---|---|---|
| *A01N 63/00* | (2006.01) | |
| *A61K 35/74* | (2015.01) | |
| *A61K 8/99* | (2006.01) | |
| *A61K 35/744* | (2015.01) | |
| *A61K 35/745* | (2015.01) | |
| *A61K 35/747* | (2015.01) | |
| *A61Q 5/02* | (2006.01) | |
| *A61Q 17/00* | (2006.01) | |
| *A61Q 19/00* | (2006.01) | |
| *A61Q 19/10* | (2006.01) | |

(52) U.S. Cl.
CPC . *A61K 35/74* (2013.01); *A61K 8/99* (2013.01); *A61K 35/744* (2013.01); *A61K 35/745* (2013.01); *A61K 35/747* (2013.01); *A61Q 5/02* (2013.01); *A61Q 17/005* (2013.01); *A61Q 19/00* (2013.01); *A61Q 19/10* (2013.01); *A61Q 19/005* (2013.01); *A61Q 19/008* (2013.01)

(58) Field of Classification Search
None
See application file for complete search history.

(56) References Cited

U.S. PATENT DOCUMENTS

| | | |
|---|---|---|
| 4,464,362 A | 8/1984 | Kludas et al. |
| 5,324,515 A | 6/1994 | Lee et al. |
| 5,494,664 A * | 2/1996 | Brassart et al. ............... 424/93.4 |
| 5,578,302 A | 11/1996 | Brassart et al. |
| 5,603,930 A | 2/1997 | Brassart et al. |
| 5,614,209 A * | 3/1997 | Ford ............................ 424/443 |
| 5,633,012 A | 5/1997 | Ford |
| 5,635,202 A | 6/1997 | Ford |
| 5,656,268 A * | 8/1997 | Sorodsky ................... 424/93.45 |
| 5,733,568 A | 3/1998 | Ford |
| 5,981,261 A | 11/1999 | Mollet et al. |
| 6,270,811 B1 | 8/2001 | Fregonese |
| 6,645,506 B1 | 11/2003 | Farmer |
| 2005/0180961 A1 | 8/2005 | Pecquet et al. |

FOREIGN PATENT DOCUMENTS

| | | |
|---|---|---|
| EP | 0577903 | 1/1994 |
| EP | 0904784 | 3/1999 |
| WO | WO9638159 | 12/1996 |
| WO | WO9736603 | 10/1997 |
| WO | WO9847374 | 10/1998 |
| WO | WO9917788 | 4/1999 |

OTHER PUBLICATIONS

Reid et al., Journal of Industrial Microbiology (1995, 15,248-253.*
Bernet-Camard et al., 1994 Gut 35:483-489.*
English abstract of JP 09263539—Oct. 7, 1997.
English abstract of JP 5017363—Jan. 26, 1993.
English abstract of JP 9002959—Jan. 7, 1997.
English abstract of JP 63179829—Jul. 23, 1988.
English abstract of CN 1110147—Oct. 18, 1995.
Reid et al., Journal of Industrial Microbiology (1995) 15, 248-253.
Doern et al., Diagn Microbiol Infect Dis 1999;34:65-72.
http://www.attc.org/ATCCAdvancedCatalogSearch/ProductDetails/tabid/452/Default.aspx (accessed Sep. 10, 2009).
Duez et al., Journal of Applied Microbiology 2000, 88, 1019-1027.
Haschke et al., Monatsschr Kinderheilkd,1998 o [Suppl 1] 146:S 26-30.
Pridmore et al., Applied and Environmental Microbiology, May 1996, p. 1799-1802 vol. 62, No. 5.

* cited by examiner

*Primary Examiner* — Irene Marx
(74) *Attorney, Agent, or Firm* — K&L Gates LLP

(57) ABSTRACT

Bacterial agents for preparing compositions which are for cosmetic, pharmaceutical or veterinary use and which are intended to stabilize and/or regulate the cutaneous ecosystem of mammals. These bacterial agents being an extract of a bacterium, or a bacterium, selected for their adhesion to skin cells and anti-adhesive to pathogens of the cutaneous system. The invention also relates to compositions containing such agents.

6 Claims, No Drawings ued States Patent

LACTOBACILLUS JOHNSONII CNCM I-1225 FOR THE ANTI-ADHESION OF SKIN PATHOGENIC FLORA

CROSS REFERENCE TO RELATED APPLICATIONS

This application is a continuation application of U.S. patent Ser. No. 11/217,930, filed Sep. 1, 2005, now U.S. Pat. No. 8,685,389, which is a divisional of U.S. patent application Ser. No. 10/177,589, filed Jun. 21, 2002 (abandoned), which is a continuation of International application PCT/EP00/12719 filed Dec. 13, 2000, which claims priority to EP99204489.1, filed Dec. 22, 1999, the entire content of which is expressly incorporated herein by reference.

TECHNICAL FIELD

The present invention relates to the use of a bacterial agent selected for its properties of anti-adhesion of skin pathogens, for the preparation of compositions which are for cosmetic, pharmaceutical or veterinary use and which are intended to stabilize and/or regulate the cutaneous ecosystem of mammals, and to the compositions containing such an agent.

BACKGROUND ART

The proliferation of pathogens such as *Staphylococcus aureus, Streptococcus pyogenes* or *Propionibacterium acnes*, or of certain yeasts, can lead to dysregulation of the cutaneous system, or even more serious disorders of skin or of mucous membranes, such as eczema, candidiases, dermatitises, etc.

Many means of treatment against these pathogenic agents are known. The most conventionally used are antibiotics or chemical antibacterial agents. They are, for example, compositions based on aldehydes and derivatives.

Thus, the published patent application FR 2740039 describes the use of a substance chosen from aldehydes and bifunctional compounds, preferably glutaraldehyde, for inhibiting the attachment of strains of pathogens such as *Staphylococcus aureus* to keratinocytes and corneocytes.

Thus, hexachlorophene and its derivatives are known as antibacterial substances and are more particularly used against *Propionibacterium acnes*.

However, these treatments are in general expensive and harmful to both the health and the environment. Alternative, nontoxic treatments are now known which consist in using the antifungal, bactericidal or bacteriostatic properties of certain strains of microorganisms.

Thus, PCT application WO 97/366603 demonstrates the antifungal properties of a strain of *Lactobacillus casei*.

Other bacterial agents, such as the *Bacillus*, can also be used on skin or mucous membranes. Specifically, in application WO 98/47374, strains of *Bacillus coagulans, Bacillus subtilis, Bacillus laterosporus* and *Bacillus laevolacticus* are used in compositions intended to prevent bacterial, viral or fungal infections of skin or of mucous membranes.

The invention proposes to find a novel bacterial agent capable of controlling and regulating the cutaneous ecosystem in order to improve upon the deficiencies of the prior art.

SUMMARY OF THE INVENTION

The present invention relates to the use of a bacterial agent for preparing a composition which is for cosmetic, pharmaceutical or veterinary use and to the resulting compositions. These compositions are intended to be administered to humans or to animals for the purpose of preventing or treating disorders induced by pathogens of the cutaneous system. The bacterial agent is generally an extract of a lactic acid bacterium, or a lactic acid bacterium, and is selected for its properties of adhesion to skin cells as well as for regulation of the attachment of skin pathogens, in particular by inhibiting their adhesion.

Suitable bacterial agents may be selected from strains of *Lactobacillus, Micrococcus* or *Bifidobacterium*, and preferably from the *Lactobacillus johnsonii* CNCM I-1225, *Micrococcus varians* CNCM I-1586, *Micrococcus varians* CNCM I-1587 or *Bifidobacterium animalis* ATCC 27536 strains.

The bacterial strain can be used in a viable, deactivated or semi-active form. It also can be used in the form of a lyophilized powder, which can, e.g., comprise approximately $10 \times 10^8$ to $10 \times 10^{11}$ cfu/g.

The composition of the present invention are intended for cosmetic, pharmaceutical or veterinary use and contains at least one bacterial agent capable of stabilizing and/or of regulating the pathogenic flora of the cutaneous system. As noted above, the bacterial agent is an extract of a bacterium, or a bacterium, selected for its properties of adhesion with respect to skin cells and its anti-adhesive properties with respect to pathogens of the cutaneous system.

These compositions can also be used in ophthalmology or for nasal application. Also, they can in particular be in the form of a cream, lotion, hypoallergenic cleansing bar, shampoo or powder.

DETAILED DESCRIPTION OF THE PREFERRED EMBODIMENTS

In this invention, skin cells (i.e. keratinocytes) as well as corneocytes are grouped together under the name "cutaneous system".

The present invention provides a bacterial agent selected for its property of adherence to skin cells, and of stabilization and regulation of the pathogenic bacterial flora of the cutaneous system, in particular by inhibiting the adhesion of pathogens such as *Staphylococcus aureus, Streptococcus pyogenes* or *Propionibacterium acnes*. For this, many bacterial strains were tested for their properties of attachment to human keratinocytes (cf. Example 1).

From diverse bacterial strains thus tested, strains of *Lactobacillus*, of *Micrococcus* and of *Bifidobacterium* have been found to be useful, with a stain of *Lactobacillus johnsonii* (NCC 533), two strains of *Micrococcus varians* (NCC 1482, NCC 1520) and a strain of *Bifidobacterium animalis* (ATCC 27536) being preferred for selection as the agent.

The strain of *Lactobacillus johnsonii* (NCC 533) and the strains of *Micrococcus varians* (NCC 1482 and NCC 1520) were deposited, according to the Treaty of Budapest, at the Collection Nationale de Cultures de Microorganismes (CNCM) [National Collection of Microorganism Cultures], Institut Pasteur, 28 rue du Docteur Roux, 75724 Paris Cedex 15, France, respectively on 30 Jun. 1992 under the reference CNCM I-1225 for *Lactobacillus johnsonii*, and 7 Jun. 1995 under the references CNCM I-1586 and CNCM I-1587 for *Micrococcus varians* NCC 1482 and NCC 1520.

The strain of *Bifidobacterium animalis* (ATCC 27536) can be obtained from Hansen (Chr. Hansen A/S, 10-12 Boege Alle, P.O. Box 407, DK-2970 Hoersholm, Denmark).

Details concerning the morphology and the general properties of the strains are given below:

*Lactobacillus johnsonii* CNCM I-1225
Morphology
    Non-motile Gram-positive microorganism which does not form spores.
    Fairly short and squat isolated rods.
Metabolism
    Microaerophilic microorganism with homofermentative metabolism giving rise to the production of L (+) and D (−) lactic acid.

Other characteristics: Catalase (−), $CO_2$ production (−), arginine hydrolysis (−).

Fermentation of sugars:

Amygdalin (+), arabinose (−), cellobiose (+), esculin (+), fructose (+), galactose (−), glucose (+), lactose (+), maltose (+/−), mannitol (−), mannose (+), melibiose (−), raffinose (+), ribose (−), salicine (+), sucrose (+), trehalose (+).

*Micrococcus varians* CNCM I-1586 (NCC 1482) and CNCM I-1587 (NCC 1520)

Morphology
Gram-positive microorganism, is permanently immobile.
Spherical form, is in the form of irregularly arranged tetrades.

Metabolism
Aerobic microorganism, catalase (+)
Other characteristics: yellow colour on BHI medium. The optimum growth temperature of said strains is 25-37° C.

Fermentation of sugars
Fructose (+), glucose (+).

The bacteria according to the invention are used for preparing compositions intended for the prophylaxis or the treatment of disorders linked to pathogens of the cutaneous system, such as *Staphylococcus aureus, Streptococcus pyogenes* or *Propionibacterium acnes*, or yeasts. These skin disorders can be in particular atopic dermatitis (in the remission phases, as a maintenance treatment), acne, candidiases, seborrhoeic dermatitis, pityriasis versicolor, impetigo or eczematous secondary infections.

The disorders of the cutaneous system may also be linked to therapies with antibiotics or antimycotic agents, to diabetes (candidiases), to a pathology of mucous membranes (vaginal candidiasis), to chronic eczema (homeostasis imbalance), to sensitive skin (premature babies, children) or greasy skin (linked to hormonal dysregulation which may promote the growth of bacteria) or to dandruff.

The bacteria according to the invention can be used in their live or semi-active form, or in a deactivated form. The expression "bacterium in a semi-active form" is intended to mean a bacterium with low physiological activity. This activity can be measured by a longer exponential growth phase or generation time, a metabolism which has slowed or an incomplete physiological response to modifications of the environment, for example. In certain extreme cases, the number of bacteria may be decreased since they can no longer withstand the change in the environment.

Bacterial culture supernatants can also be used successfully in this invention.

According to a first embodiment of the invention, the bacterial agent can be an extract of a bacterium, or a bacterium, said bacterium being in its viable active form. The bacterial agent is then preferably converted into a lyophilized powder, for example, according to the method described in EP 818529. The powder can contain from $10\times10^8$ to $10\times10^{11}$ cfu/g.

According to another embodiment, the bacterial agent can be an extract of a bacterium, or a bacterium, in a semi-active form. The partial deactivation of the strains can be carried out in several ways, in particular by:

freeze drying, consisting of cycles of freezing in liquid nitrogen/thawing at 37° C. A decrease of approximately 1 log can then be obtained, the action of UV rays (15 to 60 minutes at 254 nm, distance 20 cm): decrease of 2 to 3 logs, the action of heat (70° C. for 3 hours): decrease of approximately 3 to 4 logs, for example.

The bacterial agent can then be used in the form of a powder containing at least $10\times10^6$ cfu/g, and preferably in dry compositions, such as dry shampoos or other powder compositions, which can contain up to 10% of the bacterial extract.

Finally, the bacterial agent can also be an extract of a bacterium, or a bacterium, in a deactivated form. The bacterium is preferably inactivated by heat treatment at approximately 90° C. for approximately 2 hours. The bacterial agent is in the form of a lyophilized powder containing from $10\times10^8$ to $10\times10^{12}$ cfu/g. It can be used at up to 5%, and from preferably from 0.05 to 3%, in liquid compositions and at up to 10% in pulverulent compositions.

The present invention also relates to a composition which is for cosmetic, pharmaceutical or veterinary use and which contains a bacterial agent having the properties as described above.

In order to prepare such a composition, at least one bacterial strain in viable, semi-active or deactivated form is incorporated into a pharmaceutically or cosmetically acceptable support in an amount which varies as a function of the desired use. The bacterial agent can be present at up to approximately 5% with respect to the total weight of the composition and at up to 10% for compositions in the form of a powder, and preferably at between 0.5 to 2%.

The compositions according to the invention can be administered via the topical or ocular route.

Via the topical route, the pharmaceutical compositions based on compounds according to the invention are preferably intended for the treatment of skin and of mucous membranes, and can be in the form of salves, of creams, of milks, of ointments, of powders, of soaked swabs, of solutions, of gels, of sprays, of lotions or of suspensions. They can also be in the form of microspheres or nanospheres, or lipid or polymeric vesicles, or of polymer patches and of hydrogels, which allow controlled release. These compositions for administration via the topical route can be either in anhydrous form or aqueous form, depending on the clinical indication.

Via the ocular route, they are mainly eyewashes.

In a preferred embodiment, the invention relates to a cosmetic composition containing, in a cosmetically acceptable support, at least one bacterial agent as defined above. The cosmetic composition can contain the bacterial agent in a proportion of at least 0.001% by weight with respect to the total weight of the composition, and preferably from 0.05 to 3%.

This cosmetic composition is in particular intended for body and hair hygiene. It can in particular be in the form of a cream, a milk, a lotion, a gel, microspheres or nanospheres, or lipid or polymeric vesicles, a soap or a shampoo.

In the compositions according to the invention, the viable or inactivated bacterial agent can be combined with retinoids or corticosteroids, or combined with anti-free radicals, with α-hydroxy or α-keto acids or their derivatives, or with ion channel blockers.

The pharmaceutical and cosmetic compositions according to the invention can also contain inert additives or even pharmacodynamically or cosmetically active additives, or combinations of these additives, and in particular: wetting agents; depigmenting agents such as hydroquinone, azelaic acid, caffeic acid or kojic acid; emollients; moisturizing agents such as glycerol, PEG-400, thiamorpholinone and its derivatives, or urea; anti-seborrhoeic or anti-acne agents, such as S-carboxymethylcysteine, S-benzylcysteamine, their salts and their derivatives, or benzoyl peroxide; antibiotics such as erythromycin and its esters, neomycin, clindamycin and its esters; tetracyclins; antifungal agents such as ketoconazole or 4,5-polymethylene-3-isothiazolinones; agents for promoting the regrowth of hair, such as Minoxidil (2,4-diamino-6-piperidinopyrimidine 3-oxide) and its derivatives, Diazoxide (7-chloro-3-methyl-1,2,4-benzothiadiazine 1,1-dioxide) and Phenyloin (5,4-diphenylimidazolidine-2,4-dione); [sic], non-steroidal anti-inflammatory agents; carotenoids and, in particular, β-carotene; anti-psoriatic agents such as anthraline and its derivatives; and finally, eicosa-5,8,11,14-tetraynoic acid and eicosa-5,8,11-trynoic acid, their esters and amides.

The composition according to the invention can also contain preserving agents such as para-hydroxybenzoic acid esters, stabilizers, moisture regulators, pH regulators, osmotic pressure modifiers, emulsifying agents, UV-A and UV-B screening agents, and antioxidants such as α-tocopherol, butylhydroxyanisole or butylhydroxytoluene.

Finally, the present invention also relates to a composition which is for veterinary or cosmetic use for animals and which contains at least one bacterial agent as defined above. Such a composition can be in the form of dry or liquid shampoos, powders, foams or lotions, for example. It can contain up to 10% of the bacterial agent.

The composition according to the invention is intended in particular for the therapeutic or prophylactic treatment of healthy, sensitive and/or diseased skin and/or mucous membranes which may exhibit disorders of the cutaneous system, such as in particular:

infectious complications such as superinfected atopic dermatitis, impetigo-based eczema, ulcers, wounds, burns, superinfected inflammatory acne, dermatitises such as impetigo, superficial folliculitis, seborrhoeic dermatitises, pityriasis versicolor, dermatophytoses (Tinea capitis, Tinea corporis, athlete's foot, Hebra's eczema, herpes carcinatus), candidiases (vaginal, interdigital, linked to professions at risk or to diabetes), disorders linked to therapies with antibiotics or to antimycotic agents, disorders caused by hormonal dysregulation (greasy skin) or linked to dandruff, sensitive skin (premature babies, children).

The compositions for veterinary use are particularly intended to treat or prevent dysfunctions due to staphylococcal infections (due to *Staphylococcus aureus, S. intermedians*), streptococcal infections (due to *S. pyogenes*) and mycotic infections (candidoses due to *C. albicans* and pytirosporoses due to *P. canis*).

EXAMPLES

Other characteristics of the present invention will appear in the course of the following descriptions of examples of embodiments, which are provided for the purposes of illustrating the present invention but no to limit it.

Example 1

Selection of the Bacterial Agent

In the context of the present invention, the adhesion of 12 different bacterial strains to skin cells, in particular to HaCat human keratinocytes in culture, is studied. These strains belong to the *Lactobacillus, Bifidobacterium, Micrococcus, Staphylococcus, Streptococcus* and *Propionibacterium* genera.

The bacterial cultures (1 ml) are incubated in 10 ml of medium (cf. Table 1) overnight. For the adhesion assays, the bacteria are precultured until a concentration of $5.0 \times 10^8$ to $10^9$ cfu/m$^1$ is obtained. The cfu are standardized by measuring the optical density of each strain (OD at $10^8$ cfu/ml: see Table 1).

Then, the bacterial strains are assayed for their adhesion properties.

TABLE 1

Bacterial strains and culture conditions

| Bacterial strains | NCC Code | Medium | Incubation T° C./hour | OD at $10^2$ cfu |
|---|---|---|---|---|
| *Lactobacillus johnsonii* La1 | 533 | MRS | Anaerob. 37° C./48 h | 1.00 |
| *Lactobacillus acidophilus* La10 | 90 | MRS | Anaerob. 37° C./48 h | 1.00 |
| *Bifidobacterium animalis* ATCC27536 | 536 | MRS | Anaerob. 37° C./18 h | 0.65 |
| *Bifidobacterium longum* B28 | 585 | MRS | Aerob. 30° C./18 h | 1.32 |
| *Micrococcus varians* NCC 1482 | 1482 | BHi | Aerob. 30° C./18 h | 4.85 |
| *Micrococcus varians* NCC 1520 | 1520 | BHi | Aerob. 30° C./18 h | 3.47 |
| *Micrococcus varians* MCV 17 | 1583 | BHi | Aerob. 30° C./18 h | 4.18 |
| *Staphylococcus carnosus* STC 21 | 931 | BHi | Aerob. 30° C./18 h | 40.20 |
| *Staphylococcus piscifermentans* STF4 | 751 | BHi | Aerob. 30° C./18 h | 3.26 |
| *Streptococcus thermophilus* Sfi 16 | 2019 | HJL | Aerob. 40° C./18 h | 0.37 |
| *Propionibacterium shermanii* PP12 | 1197 | MRS | Aerob. 30° C./24 h | 0.18 |
| *Propionibacterium thoenii* PP22 | 1116 | MRS | Aerob. 30° C./24 h | 0.25 |

NCC 533, NCC 90, NCC 536 and NCC 585 were cultured under anaerobic conditions (Gaspack $H_2 + CO_2$).

Human Keratinocyte Lines:

The adhesion properties of the bacteria were studied on 3 keratinocyte lines:

SV40 T-Ag immortalized cell lines: DK2-NR and FK2-NR cells as described in EP 780 469 and, HPV (Human papilloma virus) E6/E7 and SV40 T-Ag immortalized cell lines: DK7-NR cell lines as described in application WO 99/02347.

Culture Medium for the Cell Lines:

DK7-NR, FK2-NR: NR-2 (Biofluids, Rockville, Md. 20850) (EP 780469).

DK2-NR: NR-M (Biofluids, Rockville, Md. 20850).

The keratinocyte lines are cultured in a proportion of $5 \times 10^5$ keratinocytes/cm$^2$, seeded in coated 6-well clusters (Becton Dickinson, Lincoln Park, N.J.). The coating solution consists of basic medium supplemented with 10 μg/ml of human fibronectin (Becton Dickinson), 31 μg/ml of bovine collagen I (Vitrogen, Collagen Corporation, Fremont, Calif.) and 0.1 mg/ml of BSA (Biofluids, Rockville, Md. 20850). After 6 to 8 days, the cell cultures form a monolayer (confluent). Next, the $Ca^{2+}$ concentration of the medium is brought to 1.5 mM so as to induce cell differentiation. The cells are cultured for 4 days in a high calcium concentration medium, without antibiotics. For the adhesion assays, the cell cultures are washed 3 times with buffer (HBSS, $Ca^{2+}$: 1.0 mM).

Radiolabelling

The bacterial strains are labelled overnight by adding 100 μCi/10 ml of $2^{-3}H$-adenine (Amersham, TRK.311) to the culture medium. Aliquot fractions of the bacteria are incubated in a medium without $^3H$-adenine. The unlabelled (cold) supernatant is set aside in order to adjust the cfu/ml for the adhesion assays.

Adhesion Assays

The bacterial suspensions are centrifuged for 10 minutes are 4000 rpm. Before adjusting the optical density (OD), the pellets are washed twice in HBSS. The OD is measured for each strain so as to adjust the final concentrations of bacteria to $10^6$, $10^7$, $10^8$ and $10^9$ cfu/ml. The medium for the adhesion assays is a 1:1 mixture of keratinocyte culture medium and of the unlabelled supernatant of the bacterial medium.

In order to analyse the adhesion properties of the bacteria on a substrate without keratinocytes, the bacterial suspensions are incubated on plastic dishes and plastic dishes coated with cells.

Analysis

After washing the cultures 3 times with HBSS ($Ca^{2+}$, 1.0 mM), the bacteria associated with the keratinocytes are lysed in a solution of 1N NaOH for 30 minutes at room temperature. The solution is transferred into scintillation vials with 1 ml of benzethonium hydroxide (Sigma, St. Louis, USA). After 1 h at 60° C., the $^3H$ activity of the label bacteria is measured by liquid scintillation counting (dpm).

The adhesion index (AI) is calculated as $^3H$ activity (dpm/well), as % of the total $^3H$ activity (dpm/ml) of the bacterial suspension.

Results

Adhesion Index (AI)

The adhesion index of the 13 different bacterial strains is calculated by measuring the $^3H$-adenine activity of the radiolabelled microorganisms. The results are given in Table 2.

TABLE 2

Adhesion index of bacterial strains of FK2-NR keratinocytes.

| NCC Code | CFU/ml | dpm ($\times 10^3$) | =SD | Adhesion index (% of total dpm) |
|---|---|---|---|---|
| 533 | $10^9$ | 209.6 | 24.2 | 1.2 |
|  | $10^8$ | 175.5 | 42.5 | 10.4 |
|  | $10^7$ | 39.5 | 1.9 | 23.3 |
|  | $10^6$ | 4.7 | 0.3 | 27.7 |
| 90 | $10^9$ | 167.7 | 19.4 | 2.8 |
|  | $10^8$ | 47.7 | 2.9 | 7.9 |
|  | $10^7$ | 8.3 | 0.5 | 13.8 |
|  | $10^6$ | 0.9 | 0.1 | 15.5 |
| 536 | $10^9$ | 413.9 | 91.7 | 4.8 |
|  | $10^8$ | 221.0 | 31.3 | 25.5 |
|  | $10^7$ | 22.3 | 3.8 | 25.8 |
|  | $10^6$ | 2.4 | 0.3 | 28.2 |
| 585 | $10^9$ | 107.7 | 21.0 | 1.2 |
|  | $10^8$ | 19.6 | 1.5 | 2.2 |
|  | $10^7$ | 9.7 | 1.9 | 10.8 |
|  | $10^6$ | 1.3 | 0.1 | 14.3 |
| 1482 | $10^9$ | 6147.2 | 1292.6 | 72.4 |
|  | $10^8$ | 257.7 | 52.6 | 30.3 |
|  | $10^7$ | 10.4 | 0.8 | 12.3 |
|  | $10^6$ | 1.7 | 0.2 | 19.7 |
| 1520 | $10^9$ | 121.2 | 22.3 | 1.5 |
|  | $10^8$ | 40.1 | 5.7 | 5.0 |
|  | $10^7$ | 16.5 | 5.5 | 20.7 |
|  | $10^6$ | 2.3 | 0.2 | 29.0 |
| 1583 | $10^9$ | 41.3 | 9.7 | 0.7 |
|  | $10^8$ | 12.9 | 1.3 | 2.2 |
|  | $10^7$ | 7.5 | 0.5 | 12.7 |
|  | $10^6$ | 1.1 | 0.1 | 18.7 |
| 751 | $10^9$ | 195.5 | 96.5 | 2.6 |
|  | $10^8$ | 24.7 | 4.9 | 3.2 |
|  | $10^7$ | 4.8 | 0.9 | 6.4 |
|  | $10^6$ | 0.6 | 0.09 | 8.9 |
| 931 | $10^9$ | 16.2 | 2.9 | 0.5 |
|  | $10^8$ | 4.6 | 0.6 | 1.3 |
|  | $10^7$ | 1.6 | 0.1 | 4.6 |
|  | $10^6$ | 0.2 | 0.01 | 6.7 |
| 2019 | $10^8$ | 67.5 | 1.4 | 1.4 |
|  | $10^7$ | 10.0 | 0.4 | 2.1 |
|  | $10^6$ | 1.1 | 0.1 | 2.4 |
| 1197 | $10^9$ | 20.2 | 3.1 | 0.2 |
|  | $10^8$ | 3.2 | 0.2 | 0.3 |
|  | $10^7$ | 0.5 | 0.2 | 0.4 |
|  | $10^6$ | 0.1 | 0.02 | 0.6 |
| 1116 | $10^9$ | 34.1 | 2.0 | 0.2 |
|  | $10^8$ | 6.3 | 0.2 | 0.4 |
|  | $10^7$ | 0.7 | 0.1 | 0.5 |
|  | $10^6$ | 0.1 | 0.01 | 0.7 |

The results show that the highest adhesion indices are obtained for the following strains: a *Bifidobacterium animalis* ATCC 27536, a *Lactobacillus johnsonii* NCC 533 (CNCM I-1225) strain and the *Micrococcus varians* NCC 1482 (CNCM I-1586), NCC 1520 (CNCM I-1587) and NCC 1583 strains.

Example 2

In Vitro Assays of the Inhibition of the Adhesion of *Staphylococcus aureus* and *Streptococcus pyogenes* by *Micrococcus varians* NCC 1482 or *Lactobacillus johnsonii* NCC 533

Microorganisms and Culture Methods

The pathogens *Staphylococcus aureus* and *Streptococcus pyogenes* are cultured in broth by subculturing from a culture in the exponential growth phase (Table 3). An OD/bacterial density correspondence was established for each of the microorganisms assayed, on the basis of cereal dilutions and counting on agar medium.

TABLE 3

| Bacterial strain | Ref. | Medium | Culture conditions |
|---|---|---|---|
| *Staphylococcus aureus* | ATCC 6538 | TCS | Aerobiosis, 35° C./24 h |
| *Streptococcus pyogenes* | CIP 5641 T | BHI | Aerobiosis, 35° C./24 h |

Culture Medium:
TCS (AES, Combourg, ref. AEB 141502)
BHI (UNIPATH SA, Dardilly, ref. CM 225)

Transformed Human Keratinocytes

Immortalized human keratinocytes of the HaCaT line are used (Boukamp P. et al., *J. Cell Biol.*, 106, 761-771, 1988). The HaCaT cells are cultured in DMEM medium supplemented with 10% of foetal calf serum, at 37° C. under 5% of $CO_2$.

6-well clusters (Becton Dickinson) are seeded in a proportion of $10^4$ cells/cm$^2$. After 4 to 5 days, the cells reach confluence. The adhesion assays are carried out 4 to 5 days after confluence. The monolayers are washed 3 times with PBS before these assays.

Radiolabelling

The bacteria are labelled with 2-$^3$H-adenine (Amersham, TRK 311), in a proportion of 100×Ci/10 ml of broth. The suspensions are washed 3 times and then resuspended in PBS. The cell density is adjusted in this same buffer.

Adhesion Assay on Keratinocytes in Culture:

1 ml of radiolabelled bacterial suspension is incubated for 1 h at 35° C. The monolayer is washed 3 times with PBS buffer and lysed by adding 1N NaOH for 30 minutes at room temperature. The lysate is transferred into a scintillation vial and incubated for 1 h at 60° C. with 1 ml of hyamine hydroxide (Carlo Erba, ref. 464951). The $^3$H activity is counted in a liquid scintillation counter. Each assay is carried out in triplicate. A control with the plastic support is also carried out.

The adhesion is defined by the ratio between radioactivity which has adhered and radioactivity which was introduced, multiplied by 100.

Adhesion Inhibition Assay

After washing and resuspension in PBS, the radiolabelled pathogen and the cold bacterial strain are incubated simultaneously with the monolayer. The assays are carried out in triplicate for bacterial agent densities covering 3 logs.

Results

*Staphylococcus aureus, Streptococcus pyogenes, Lactobacillus johnsonii* NCC 533 and *Micrococcus varians* NCC 1482 were assayed for their adhesion to HaCaTen keratinocytes in culture. The results are given in Table 4.

TABLE 4

| Microorganism | Adhesion (%) | | |
|---|---|---|---|
| | $10^6$ cfu/ml | $10^7$ cfu/ml | $10^8$ cfu/ml |
| *Staphylococcus aureus* | — | 5.0 | 2.5 |
| *Streptococcus pyogenes* | — | 35 | 42.5 |
| NCC 533 | 4.5 | 1.7 | 1.2 |
| NCC 1482 | 6.5 | 3.0 | 0.6 |

| | Inhibition (%) | | |
|---|---|---|---|
| | $9.0 \times 10^6$ cfu/ml | $9.0 \times 10^7$ cfu/ml | $9.0 \times 10^8$ cfu/ml |
| *S. aureus* $10^8$ cfu/ml + NCC 1482 | 5 | 11 | 66 |
| *S. aureus* $10^8$ cfu/ml + NCC 533 | 20 | 24 | 34 |
| *S. pyogenes* $10^8$ cfu/ml + NCC 1482 | 26 | 28 | 40 |
| *S. pyogenes* $10^8$ cfu/ml + NCC533 | 12 | 19 | 52 |

The results show that *Staphylococcus aureus, Streptococcus pyogenes, Lactobacillus johnsonii* NCC 533 and *Micrococcus varians* NCC 1482 adhere to the keratinocytes in culture. When the density of the bacterial agent increases, the pathogen is increasingly displaced.

Example 3

In Vitro Assays of the Inhibition of the Adhesion of *S. aureus* by Active or Deactivated *Lactobacillus johnsonii* NCC 533

The in vitro adhesion model is based on the incubation of a radiolabelled and calibrated suspension of a skin pathogenic microorganism (*Staphylococcus aureus*) with a monolayer of immortalized human keratinocytes (HaCaT line) (Boukamp P. et al., *J. Cell Biol.*, 106, 761-771, 1988).

The inhibitory activity of the bacterial agent (*Lactobacillus johnsonii* NCC 533 in a viable or deactivated form) with respect to this adhesion is evaluated in the context of a co-incubation, on the monolayer, of the pathogen and of the compound to be assayed, by measuring the radioactivity retained on the monolayer.

Keratinocytes

For this, the HaCaT cells are cultured in DMEM supplemented with 10% of foetal calf serum, at 37° C. under 5% of $CO_2$. They are seeded in 6-well clusters in a proportion of $10^4$ cells/cm$^2$. The adhesion assay is carried out 5 days after confluence. The monolayers are washed 3 times with PBS before incubation with the microorganisms.

Microorganisms

*Staphylococcus aureus* (ATCC 6538) is cultured in TCS medium, in aerobiosis at 35° C.

*Lactobacillus johnsonii* NCC 533 is cultured in MRS medium, in anaerobiosis at 37° C. For the adhesion inhibition assay, a concentrated suspension of the bacterium is prepared in PBS buffer, from a 48-hour culture. The suspension is adjusted to $2 \times 10^8$ cfu/ml (OD at 525 nm=1.5). Serial dilutions are prepared in PBS buffer in order to obtain suspensions at $2.0 \times 10^7$ and $2.0 \times 10^6$ cfu/ml. The various suspensions are counted on MRS agar incubated in anaerobiosis at 37° C.

The deactivated form of NCC 533 is obtained by lyophilizing a dense suspension of Lactobacilli which has been subjected to several cycles of freezing in liquid nitrogen/thawing at room temperature. The preparation assayed corresponds to a biomass of $4.0 \times 10^{10}$ cfu/g.

Radiolabelling

The radiolabelling of *Staphylococcus aureus* is obtained by incorporating 100 μCi/10 ml of $^3$H adenine during 24 h of culturing in TCS broth. The suspension is then centrifuged for 10 minutes at 3000 rpm and washed 3 times in PBS. The cell density is adjusted with PBS buffer to approximately $2.0 \times 10^8$ cfu/ml (OD at 525 nm=0.5). The specific radioactivity is determined by scintillation counting on 100 μl of the suspension.

Adhesion Inhibition Assay:

1 ml of radiolabelled suspension of *Staphylococcus aureus* and 1 ml of suspension of NCC 533, per well of HaCaT cell culture, are simultaneously added. After 1 h of incubation at 37° C., the monolayers are washed 3 times with PBS buffer and lysed by adding 1 ml of 1N NaOH for 30 minutes at room temperature. The lysate is transferred into scintillation vials and incubated for 1 h at 60° C. with 1 ml of benzethonium hydroxide. After cooling, 10 ml of Hyonic fluor scintillation liquid are added, and the radioactivity is counted on a liquid scintillation counter. The control is obtained by adding 1 ml of radiolabelled suspension of *Staphylococcus aureus* and 1 ml of PBS buffer, and corresponds to 100% of adhesion.

The results are given in Table 5.

TABLE 5

Inhibition of the adhesion of *Staphylococcus aureus* to the HaCaT cells by NCC 533 in its viable form and in its deactivated form.

| | Adhesion (%) | Standard deviation |
|---|---|---|
| Control | 100 | 9 |
| NCC 533 $3.0 \times 10^6$ cfu/ml | 74 | 19 |
| NCC 533 $3.0 \times 10^7$ cfu/ml | 69 | 8 |
| NCC 533 $3.0 \times 10^8$ cfu/ml | 34 | 1 |
| Deactivated NCC 533 $3.0 \times 10^6$ cfu/ml | 27 | 2 |
| Deactivated NCC 533 $3.0 \times 10^7$ cfu/ml | 12 | 1 |
| Deactivated NCC 533 $3.0 \times 10^8$ cfu/ml | 6 | 0 |

Example 4

In Vivo Assays of the Inhibition of the Adhesion of Skin Pathogens by Deactivated *Lactobacillus johnsonii*

Materials and Methods

Animals:

15 7- to 8-week-old SKH female mice weighing approximately 30 g were supplied by C. River. 5 mice were used for each group assaying a different topical application.

Microorganism

A strain of *Staphylococcus aureus* (named: strain 1) which was isolated from a human skin lesion (leg ulcer) is used. This strain is sensitive to methycilin.

Preparation of the Inoculum

A suspension of the bacterium is prepared for inoculation in the mice. For this, a preculture in the exponential growth phase of strain 1 is prepared on a solid medium (AES, AEB 122 859) at 35° C. for 18 to 24 h. After incubation, the bacterium is resuspended in 10 ml of sterile saline solution, and then recovered after centrifugation at 3000 [lacuna] for 10 min. The supernatant is then removed and the pellet is taken up with 10 ml of saline solution. This procedure is repeated twice. An inoculum suspension is prepared by resuspending the washed bacteria in 4 ml of sterile saline solution. The OD at 525 nm is adjusted to approximately 0.14. It contains approximately $10^8$ cfu/ml.

Inoculation of the Mice

The skin of the mice is delipidized on the flanks with 95° [sic]ethanol (Merck). 50 µl of a suspension containing a 50/50 mixture of the *S. aureus* inoculum, $10^7$ cfu/ml, and of the product to be assayed were slowly applied to the delipidized area (6.25 cm$^2$), using a micropipette. The inoculated sites are protected by occlusion for 1 h under a sterile plastic dressing (Dermafilm 33×15, ref. 38.3015, Vygon laboratory).

Counting of the Viable Bacteria of the Lesions 4 hours after application of the suspension, the mice are killed under anaesthesia with forene (Abbott France). The inoculated sites are excised as a block (12 mm diameter). The skin biopsies removed are ground and homogenized with 2 ml of sterile saline solution, using a Polytron (PT 2100, Bioblock Scientific) (5 rpm, 5 min.).

A 1 ml sample of the homogenized tissue is added to 9 ml of a sterile saline solution, and 0.1 ml of this mixture is cultured on a staphylococcal medium No. 110 using the 10-fold dilutron method. After 48 hours of incubation at 35° C., the colonies developed are counted and the CFU (colony forming units) are determined.

Results

The results are given in Table 6.

TABLE 6

1% NCC 533 assay

| | Log cfu/cm$^2$ |
|---|---|
| *S. aureus* + PBS | 3.4 |
| *S. aureus* + 1% NCC 533 in PBS | 2.6* |
| *S. aureus* + 0.045% glutaraldehyde | 0.8* |

*significant with respect to the control (SA/PBS), Student's T test (n = 5)

The presence of NCC 533 at 1% makes it possible to decrease the number of bacteria found by approximately 1 log after 4 hours of contact. The difference appears to be significant with respect to the control (p=0.098).

In the presence of glutaraldehyde, the decrease in the number of bacteria is even more significant with respect to the control, however it is not out of the question that this activity is due to its antiseptic activity and acts as soon as the *S. aureus* is added to the mixture; thus, the activity observed after 4 h would not be due to an anti-adhesive effect, but to an antibacterial activity of the product.

The results are given in Table 7.

TABLE 7

| Inoculum size cfu/ml | Treatment | % of decrease vs. control | Significance vs. control |
|---|---|---|---|
| $10^6$ cfu/ml | 0.5% NCC 533 | 20.1% | P = 0.019 (*) |
| | 1% NCC 533 | 22.6% | P = 0.016 (*) |
| | 0.045% Glutaraldehyde | 87.9% | P = 0.0001 (***) |
| $10^7$ cfu/ml | 0.5% NCC 533 | 27.4% | P = 0.0015 (*) |
| | 1% NCC 533 | 19.9% | P = 0.0004 (***) |
| | 0.045% Glutaraldehyde | 92.0% | P = 0.0004 (***) |

(*) p < 0.05,
(***) p < 0.001 significant with respect to the control (SA/PBS)

The presence of NCC 533 at 0.5% and 1% decreases the number of *S. aureus* bacteria found by approximately 1 log for the inocula at $10^6$ cfu/ml and $10^7$ cfu/ml. No dose effect is observed, either with the $10^6$ cfu/ml inoculum or with the inoculum at $10^7$ cfu/ml.

In the presence of glutaraldehyde at 0.045%, the decrease is much greater with respect to the control; it is approximately 3 logs.

These results confirm the activity of the deactivated NCC 533 at 0.5% and 1% as an inhibitor of the adhesion of *S. aureus*.

Example 5

Body Lotion

A body lotion is prepared which has the following composition: 8.0% of mineral oil, 5.0% of isopropyl palmitate, 2.0% of polyglyceryl-3 diisostearate, 4.0% of octyldodecanol, 0.3% of carbomer, 0.2% of sodium cocoylglutamate, 1.2% of 10% sodium hydroxide, a preserving agent, fragrance, 0.5 to 3% of a lyophilisate containing from $10 \times 10^8$ to $10 \times 10^{12}$ cfu/g of at least one bacterial strain chosen from *Lactobacillus johnsonii* (CNCM I-1225), *Micrococcus varians* (CNCM I-1586 or CNCM I-1587) or *Bifidobacterium animalis* (ATCC 27536, Hansen) and inactivated by heat treatment at approximately 90° C. for about 2 hours. The mixture is made up to 100% with water.

The body lotion thus obtained is intended, due to its anti-adhesion properties with respect to pathogens, to stabilize and/or regulate skin pathogenic flora.

Example 6

Shampoo

A shampoo is prepared which has the following composition: 7.0% of sodium lauryl sulphate, 2.0% of cocamidopropyl betaine, 2.0% of sodium lauryl sulphonosuccinate, sodium chloride, preserving agent, fragrance and from 0.5 to 3% of a lyophilisate containing from $10^8$ to $10^{12}$ cfu/g of at least one bacterial strain chosen from *Lactobacillus johnsonii* (CNCM I-1225), *Micrococcus varians* (CNCM I-1586 or CNCM I-1587) or *Bifidobacterium animalis* ATCC 27536, and inactivated by heat treatment at approximately 90° C. for about 2 hours. The mixture is made up to 100% with water.

The shampoo thus prepared has properties which regulate scalp pathogenic flora. It is in particular indicated in the treatment of dandruff.

Example 7

In order to obtain a pharmaceutical composition with properties which regulate skin pathogenic flora, fatty and aqueous phases are prepared which have the following composition:

|  |  |  |
|---|---|---|
| Fatty phase: | L. johnsonii (CNCM I-1225) as described in Example 5 | 1% |
|  | Arachidyl behenyl alcohol/ arachidylglucoside | 3% |
|  | Isohexadecane | 7% |
|  | Sweet almond oil | 3% |
|  | Karite butter | 2% |
|  | B.H.T. | 0.05% |
|  | Propyl POB | 0.05% |
| Aqueous phase: | Water | Qs 100% |
|  | Glycerol | 5% |
|  | Methyl POB | 0.1% |

The fatty and aqueous phases are heated to 75° C. Then, emulsification is carried out by adding the aqueous phase to the fatty phase with Rayneri mixing at 1000 rpm. 30 minutes after the emulsification, the mixture is homogenized for 1 minute with a polytron (speed 4-5).

Example 8

In the same way as in Example 7, a composition is prepared which has the following composition:

|  |  |  |
|---|---|---|
| Fatty phase: | L. johnsonii (CNCM I-1225) as described in Example 5 | 1% |
|  | Glyceryl stearate and PEG100 stearate | 5% |
|  | Isohexadecane | 8% |
|  | Karite butter | 5% |
|  | B.H.T. | 0.05% |
|  | DC 1503 | 1% |
| Aqueous phase: | Water | Qs 100% |
|  | Glycerol | 3% |
|  | Carbopol 981 | 0.2% |
|  | Lubrajel | 5% |
|  | Phenoxyethanol | 1% |
|  | Sodium hydroxide | Qs pH 6 |

Example 9

In the same way as in Example 7, a composition is prepared which has the following composition:

|  |  |  |
|---|---|---|
|  | L. johnsonii (CNCM I-1225) as described in Example 5 | 1% |
| Fatty phase: | Polyglyceryl-3 diisostearate | 5% |
|  | Cyclomethicone CM5 | 20% |
| Aqueous phase: | Water | Qs 100% |
|  | Glycerol | 5% |
|  | NaCl | 0.5% |
|  | MgSO4 | 0.5% |

Example 10

Shampoo for Pets

A shampoo for animals is prepared which has the following composition: 5% of sodium lauryl sulphate, 2% of cocamidopropyl betaine, 2% of sodium lauryl sulphonosuccinate, 2% of sodium chloride, 1.5% of PEG-7 glyceryl cocoate, 0.75% of propylene glycol, panthenol, glycerol, disodium phosphate, preserving agent, fragrance and 1% of L. johnsonii (CNCM I-1225) as described in Example 5. The mixture is made up to 100% with water.

The shampoo thus prepared has properties which regulate the pathogenic flora of the cutaneous system of animals.

The invention is claimed as follows:

1. A method for the treatment of skin disorders caused by Staphylococcus aureus comprising: topically administering to a subject in need of such treatment a composition comprising deactivated Lactobacillus johnsonii CNCM I-1225 in an amount corresponding to $10 \times 10^8$ to $10 \times 10^{12}$ cfu/g of the composition by dry weight, wherein the Lactobacillus johnsonii CNCM I-1225 was deactivated by lyophilization of a suspension subjected to cycles of freezing in liquid nitrogen and thawing, whereby skin disorders caused by Staphylococcus aureus are treated.

2. The method of claim 1, wherein the administering comprises application to sensitive skin or greasy skin.

3. The method of claim 1, wherein the composition is a liquid.

4. The method of claim 1, wherein the composition is selected from the group consisting of a salve, a cream, a milk, a gel, a body lotion, a soap and a shampoo.

5. The method of claim 1, wherein the composition is a powder.

6. A method for inhibiting adhesion of Staphylococcus aureus to skin, the method comprising:
    topically administering to a subject in need of such treatment a composition comprising deactivated Lactobacillus johnsonii CNCM I-1225 in an amount corresponding to $10 \times 10^8$ to $10 \times 10^{12}$ cfu/g of the composition by dry weight, wherein the Lactobacillus johnsonii CNCM I-1225 was deactivated by lyophilization of a suspension subjected to cycles of freezing in liquid nitrogen and thawing, whereby adhesion of Staphylococcus aureus to skin is inhibited.

\* \* \* \* \*